United States Patent [19]

Yamamoto et al.

[11] Patent Number: 4,915,811
[45] Date of Patent: Apr. 10, 1990

[54] ELECTROPHORESIS APPARATUS

[75] Inventors: Masayoshi Yamamoto; Akira Fujita; Shoichi Yamamoto, all of Saitama, Japan

[73] Assignee: Fuji Photo Film Co., Ltd., Kanagawa, Japan

[21] Appl. No.: 208,399

[22] Filed: Jun. 17, 1988

[30] Foreign Application Priority Data

Jun. 19, 1987 [JP] Japan .................................. 62-153024

[51] Int. Cl.⁴ ....................... G01N 27/28; G01N 27/26
[52] U.S. Cl. ................................ 204/299 R; 204/182.8
[58] Field of Search .............. 204/299 R, 182.8, 182.9

[56] References Cited

U.S. PATENT DOCUMENTS 4,339,327  7/1982  Tyler ................................ 204/299 R
4,715,942 12/1987  Tezuka et al. ................ 204/182.8 X

FOREIGN PATENT DOCUMENTS 113700   8/1984  European Pat. Off. ........ 204/299 R
  3703687   8/1987  Fed. Rep. of Germany ... 204/299 R
61-278753 12/1986  Japan ............................... 204/299 R
61-278756 12/1986  Japan ............................... 204/299 R
62-220852  9/1987  Japan ............................... 204/299 R Primary Examiner—John F. Niebling
Assistant Examiner—John S. Starsiak
Attorney, Agent, or Firm—Jules E. Goldberg

[57] ABSTRACT

An electrophoresis apparatus comprises a gel sheet device composed of spacers disposed between two films at side edges thereof, a gel membrane provided within a space formed between the two films by the spacers, and sample-pouring portions provided near an upper edge of the gel membrane. Two supporting members hold the gel sheet device therebetween, and a gap-forming member contacts edges of at least one surface of the gel sheet device. Each sample-pouring portion is adapted to sample pouring into a space formed by the films, a shark's teeth comb, and the upper edge face of the gel membrane. The gap-forming member remote from an upper buffer solution vessel is provided such that an inner edge of a gap-forming member portion contacting the upper portion of the gel sheet device coincides with the upper edge face of the gel membrane, or the extent of overlapping of the gap-forming member portion upon the gel membrane is 5 mm or less.

12 Claims, 4 Drawing Sheets

ELECTROPHORESIS APPARATUS

BACKGROUND OF THE INVENTION

1. Field of the Invention

This invention relates to an electrophoresis apparatus for separating and analyzing high molecular materials, such as proteins and nucleic acids which can have an electric charge in a solution, based on differences in their molecular charges and in their molecular weights.

2. Description of the Prior Art

The electrophoresis technique has been widely known for separating and analyzing proteins, nucleic acids, their degradation products and the like based on differences in molecular charges and in molecular weights in a sheet-like medium such as a gel membrane and a filter paper containing a buffer solution.

In particular, technique for determining base sequences of radioactive-labeled nucleic acids by using autoradiography is important in the field of genetic technology. In the electrophoresis for this purpose, a base-specific reaction product (mixture) of a radioactive-labeled DNA or of a fragment of such a DNA is subjected to electrophoresis along the direction of electric field of electrophoresis medium. In general, a plurality of base-specific reaction products are migrated in parallel along the direction of electric field. After this electrophoresis, a plurality of rows of electrophoresis patterns are obtained as an autoradiographic image (autoradiogram). Then, base sequence determination is carried out by comparing and collating these patterns therebetween.

Heretofore, an experimenter of electrophoresis has had to prepare by himself a gel membrane consisting of a hydrophilic high molecular material such as starch or polyacrylamide on a flat substrate such as a glass plate on every occasion for electrophoresis. This work has been a heavy burden to the experimenter who uses electrophoresis. Recently, in order to reduce this burden, a sheet device (gel sheet device) prefabricated for electrophoresis has become commercially available in which two rectangular, electrically-insulating, flexible sheets (a support sheet and a cover sheet) are disposed face to face sandwiching therebetween a spacer of a predetermined thickness at each edge in the width direction thereof, and a gel membrane is contained within the thus formed space as an electrophoresis medium.

Before the electrophoresis is to be started, it is necessary to pour the sample liquid, which is to be subjected to electrophoresis, into the upper edge of the gel membrane (i.e. the edge that is positioned at the upper portion of a vertical electrophoresis apparatus and does not face the aforesaid spacer). Therefore, forming of a plurality of rectangular wells or slots each provided with an open end at or in the vicinity of the upper edge of the gel membrane has widely been used in practice. However, this method results in a gap of 1 mm or more formed between a pair of adjacent electrophoresis zones (lanes), corresponding to the interval between the adjacent wells.

In the base sequence determination of a DNA, where electrophoretic images of DNA-fragments containing four kinds of bases (A, G, C, T) respectively, have to be compared and collated each other, such a gap between the lanes of electrophoretic images makes the collation difficult. In order to eliminate the gap between the electrophoresis lanes, instead of providing the wells (or slots), it has been known to dispose a shark's teeth comb, which is a flat plate-like member having protrusions like shark's teeth, such that the protrusions are in contact with or partially intruded into an edge of a gel membrane, and to pour a sample liquid into a substantially triangular space (pouring aperture) formed by the edge of the gel membrane and a pair of adjacent end faces of the protrusions. If the shark's teeth comb is not inserted accurately and steadily to the predetermined position, the sample liquid will invade a neighboring pouring aperture through the gap between the gel membrane and the protrusions of the shark's teeth comb. As a result, the electrophoresis patterns overlap each other, or the electrophoretic image is distorted, so that it becomes difficult to read base sequences.

In the base sequence determination of a DNA, it is desired that as much base sequences as possible be determined on a single electrophoresis medium. Accordingly, long-term electrophoresis for determining a sequence of high molecular components (for example, the number of discernible bases is within the range of 90 to 250 for four hours at 3,000 V) and short-term electrophoresis for determining a sequence of low molecular components (for example, the number of discernible bases is within the range of 20 to 110 for two hours at 3,000 V) are often carried out sequentially on a single electrophoresis medium.

In such a case, prior to pouring of a DNA sample liquid after the completion of the long-term electrophoresis, a new sample pouring site is usually washed with a buffer solution (of the same type as the buffer solution used in an upper buffer solution vessel of an electrophoresis apparatus). At the time of the washing, the shark's teeth comb is often deviated or separated from the predetermined position, so that the electrophoretic image is often distorted and base sequences become indiscernible. In addition, the edge face of the gel membrane swells toward the sample-pouring portion in the course of the long-term electrophoresis, so that the electrophoretic image obtained by the preceding short-term electrophoresis is disturbed.

Accordingly, it is important that, when the long-term electrophoresis and the short-term electrophoresis are carried out sequentially, the shark's teeth comb does not deviate or separate from the predetermined position, and the upper edge of the gel membrane is not caused to swell by the electrophoresis carried out previously.

SUMMARY OF THE INVENTION

The primary object of the present invention is to provide an electrophoresis apparatus using an electrophoresis gel sheet device as an electrophoresis medium and using a shark's teeth comb at sample-pouring portions, wherein an electrophoretic image is prevented from being disturbed by swelling of an upper edge of a gel membrane during long-term electrophoresis and by deviation or separation of the shark's teeth comb from its normal position at the time of washing after long-term electrophoresis, when long-term electrophoresis and short-term electrophoresis are carried out sequentially.

Another object of the present invention is to provide an electrophoresis apparatus which achieves electrophoresis accurately.

The present invention provides an electrophoresis apparatus comprising:

(i) an electrophoresis gel sheet device in which gel membrane-casing spacers each having a predetermined thickness are disposed between two electrically-insulating, transparent or semitransparent films at edges in the width direction thereof, a gel membrane of a substantially uniform thickness formed of a hydrophilic high molecular material adapted to function as an electrophoresis medium is provided within the space formed between said two films by means of said spacers, and sample-pouring portions are provided in the vicinity of an upper end of said gel membrane in the length direction thereof, (ii) two electrically-insulating, flat plate-like supporting members for holding said electrophoresis gel sheet device therebetween, (iii) a gap-forming member provided in contact with peripheral edges of at least one of surfaces of said electrophoresis gel sheet device for forming a gap between at least one of said flat plate-like supporting members and said electrophoresis gel sheet device, and (iv) an upper buffer solution vessel and a lower buffer solution vessel each provided with an electrode, wherein said electrophoresis gel sheet is provided further with a shark's teeth comb attached to an edge in the vicinity of an upper end of said gel membrane prior to electrophoresis, so that said sample pouring portions are provided as spaces formed by
said films,
said shark's teeth comb and
said edge, and said gap-forming member is provided such that an inner edge thereof contacting the upper portion of said electrophoresis gel sheet device is substantially aligned with said edge face of said gel membrane forming said sample-pouring portions, or such that said gap-forming member and said gel-membrane overlap in part not more than 5 mm along the direction of electrophoresis (i.e. the longitudinal direction of the gel membrane).

With the electrophoresis apparatus in accordance with the present invention, even if long-term electrophoresis and short-term electrophoresis are carried out sequentially, electrophoretic images can be prevented from being disturbed due to deviation or separation of the shark's teeth comb from its normal position at the time of washing after long-term electrophoresis and by swelling of the upper edge of the gel membrane during long-term electrophoresis.

At the portion of the gap-forming member that contacts the upper portion of the electrophoresis gel sheet device, the extent of overlapping of the gap-forming member upon the gel membrane should preferably be 3 mm or less along the direction of electrophoresis.

The electrophoresis gel sheet device may be of any known type. For example, an electrophoresis gel sheet device comprising polyacrylamide as the electrophoresis medium disclosed in Japanese Unexamined Patent Publication No. 61(1986)-18852 is preferable. The method and apparatus disclosed in, for example, Japanese Unexamined Patent Publication No. 60(1985)-203847 can be used for making such an electrophoresis gel sheet device. However, instead of polyacrylamide gel, other materials such as agarose gel and starch may be used as the electrophoresis medium.

The basic configuration of the electrophoresis apparatus using the electrophoresis gel sheet device in accordance with the present invention may be same as that of a known vertical (upright) electrophoresis apparatus. The apparatus disclosed in Japanese Unexamined Patent Publication No. 61(1986)-278751 is one preferable example.

Glass plates are usually used as the flat plate-like supporting members for holding the electrophoresis gel sheet device therebetween to fix it to the electrophoresis apparatus. The glass plates should preferably have a flatness within the range of $\pm 10$ $\mu$m. Normally, a cutaway part is formed in one of the two glass plates to communicate the buffer solution vessel to the electrophoresis gel sheet device.

There is no particular limitation to the shapes of the protrusions (shark's teeth) of the shark's teeth comb, and any known shark's teeth comb may be used. Particularly, a shark's teeth comb having pointed tips and a shark's teeth comb having a shape proposed in Japanese Patent Application No. 61(1986)-190999 are preferable.

As the material for the shark's teeth comb, a thermoplastic synthetic or semisynthetic high-molecular material is suitable, and a polyethylene terephthalate film is preferable. Though a transparent material may be used, a semitransparent material should preferably be used so that the sample-pouring portions are easily discerned. (For example, Lumirror Film #250 S10, #250 H10 and the like manufactured by TORAY Co., Ltd. can be used preferably.)

The thickness d of the shark's teeth comb may be slightly larger than the thickness of the spacer (which, is generally thicker than the gel membrane by 10 $\mu$m to 50 $\mu$m) disposed between the support sheet and the cover sheet at their edges. However, it is desirable that the difference in their thickness does not exceed 20 $\mu$m in order to ensure insertion of the shark's teeth comb. Also, in order to prevent a sample liquid from leaking at the sample-pouring portions, the thickness d of the shark's teeth comb and the thickness G of the gel membrane should preferably satisfy the relationship of $$G \times 1.1 < d < G + 50$$

where the unit is $\mu$m. In this formula, G should be less than 500 and generally within the range of 140 $\mu$m to 400 $\mu$m.

In the electrophoresis apparatus in accordance with the present invention, the two electrically-insulating, flat plate-like supporting members are provided for holding the electrophoresis gel sheet device therebetween, and the gap-forming member is provided in contact with the peripheral edges of the electrophoresis gel sheet device for forming a gap between the electrophoresis gel sheet device and at least one flat plate-like supporting member that is disposed on the side opposite to the upper buffer solution vessel with respect to the electrophoresis gel sheet device. Specifically, as described in Japanese Patent Application No. 61(1986)-25587, in the case, where the electrophoresis gel sheet device is directly sandwiched and held between the two supporting members, the gel membrane between the films of the electrophoresis gel sheet device is compressed by small particles such as dust present, if any, between the gel sheet device and the supporting members, and thus the electrophoretic image is distorted. Therefore, the gap-forming member is provided for forming a gap between the electrophoresis gel sheet device and at least one of the two flat plate-like supporting members so as to prevent the electrophoresis gel sheet device from being depressed by particles such as dust.

The gap-forming member is a thin flexible sheet and may be formed of, for example, a polyester polymer such as polyethylene terephthalate, a polyamide polymer such as nylon, a polymer of an olefin monomer such as polyethylene, polystyrene, polyvinyl chloride or polyvinylidene chloride, a cellulose ester, glass, or a waterproof paper. The gap-forming member preferably consists of electrically-insulating material. The thickness of the gap-forming member should preferably be within the range of 0.1 mm to 0.6 mm.

The electrophoresis gel sheet device generally has a rectangular outer shape. Therefore, the gap-forming member attached to the peripheral edges of the electrophoresis gel sheet device is preferably, like a window frame, composed of a rectangular peripheral edge portion and an aperture in the central portion facing the gel membrane of the electrophoresis gel sheet device.

DESCRIPTION OF THE PREFERRED EMBODIMENTS

The present invention will hereinbelow be described in further detail with reference to the accompanying drawings.

Figure 1:
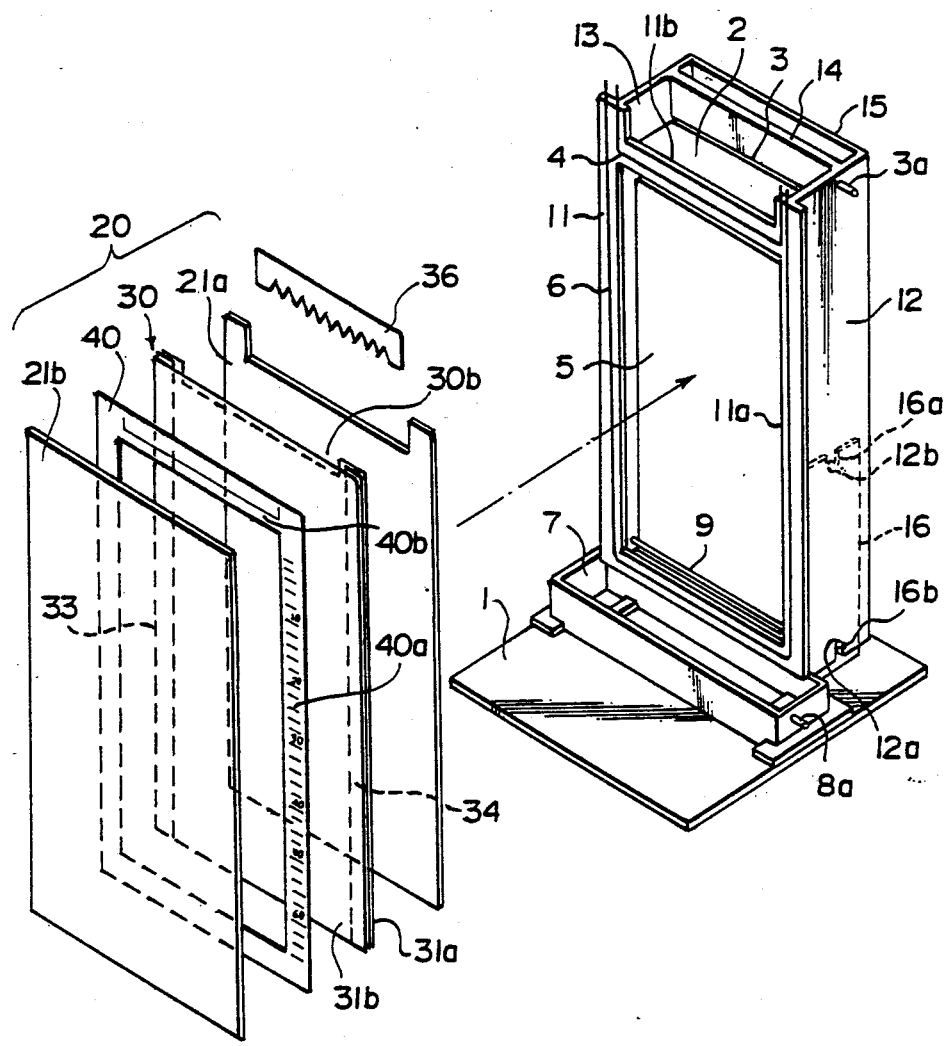
FIG. 1 is an exploded perspective view showing an embodiment of the electrophoresis apparatus in accordance with the present invention.
Figure 2:
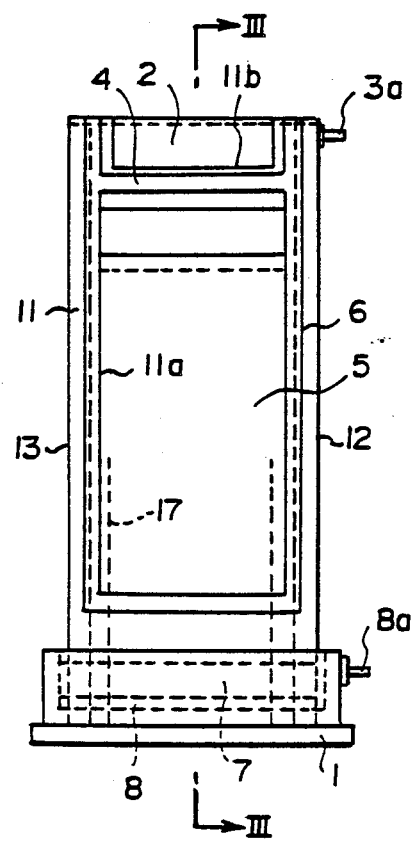
FIG. 2 is a front view showing the embodiment of FIG. 1.
Figure 3:
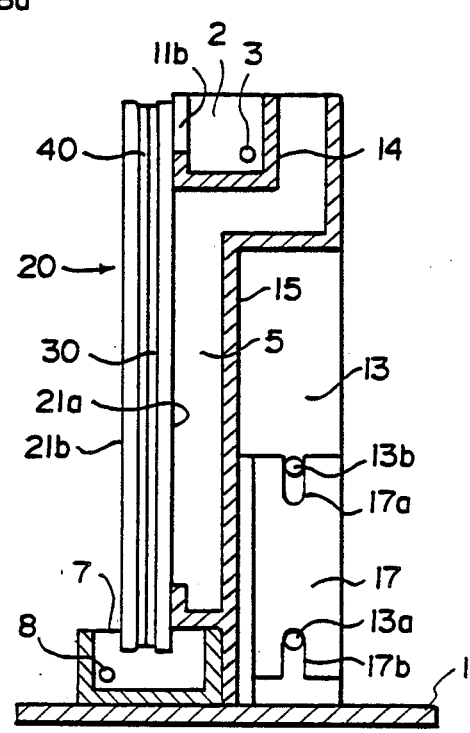
FIG. 3 is a sectional view taken along line 3—3 of FIG. 2.

With reference to FIGS. 1, 2 and 3, an embodiment of the electrophoresis apparatus is basically composed of a supporting base 1, and an upper buffer solution vessel 2, a water vessel 5, and a lower buffer solution vessel 7 which are mounted on the supporting base 1. An upper electrode 3 and a lower electrode 8 formed of a single platinum wire extending in the width direction of the apparatus are disposed in the upper buffer solution vessel 2 and the lower buffer solution vessel 7, respectively, so that the electrodes (3 and 8) are dipped in a buffer solution introduced into the respective buffer solution vessels (2 and 7). The electrodes 3 and 8 are respectively connected to external terminals 3a and 8a projecting outwardly from the side walls of the upper buffer solution vessel 2 and the lower buffer solution vessel 7, respectively.

The upper buffer solution vessel 2 is defined by side plates 12 and 13, a rear and bottom plate 14, and a front frame 11, and is formed with the upper surface open. A cutaway portion 11b is formed at the upper section of the front frame 11. The water vessel 5 extends from the rear of the upper buffer solution vessel 2 downwardly near to the lower buffer solution vessel 7. The water vessel 5 is defined by the side plates 12 and 13, a back plate 15 and the front frame 11. The side plates 12 and 13 and the front frame 11 are the parts common to the upper buffer solution vessel 2 and the water vessel 5, and thus the upper buffer solution vessel 2 and the water vessel 5 are formed integrally with each other. A front opening 11a is formed in the front surface of the water vessel 5.

The upper buffer solution vessel 2 and the water vessel 5 formed integrally with each other are held on the supporting base 1 so that the side plates 12 and 13 engage with a pair of vertical plates 16 and 17, which are secured to the upper surface of the supporting base 1, by grasping them from outside. The lower buffer solution vessel 7 is releasably held on the supporting base 1 at the position below the front frame 11.

As shown in FIG. 3, an electrophoresis sheet assembly 20 composed of flat plate-like supporting members 21a and 21b formed of glass plates, ceramic plates, or the like and an electrophoresis gel sheet device 30 of the aforesaid type sandwiched between the flat plate-like supporting members 21a and 21b is fitted to the front side of the front frame 11, and then the upper buffer solution vessel 2 and the water vessel 5 are mounted on the supporting base 1. Thus, the electrophoresis sheet assembly 20 closes the cutaway portion 11b in the front surface of the upper buffer solution vessel 2 and the front opening 11a of the water vessel 5. A buffer solution vessel packing 4 and a water vessel packing 6 are provided on the front frame 11 so that the buffer solution and water do not leak from between the contact surfaces of the electrophoresis sheet assembly 20 and the front frame 11.

The electrophoresis sheet assembly 20 will be described hereinbelow in detail. As shown in detail in FIGS. 1 and 4, the electrophoresis gel sheet device 30 is composed of sheet members 31a and 31b formed of a non-conductive organic polymer film and disposed to stand facing each other, spacers 33 and 34 having predetermined thickness and disposed along two lateral edges between the sheet members 31a and 31b, and an electrophoresis gel membrane 35 having a uniform thickness and disposed between the sheet members 31a and 31b. As the sheet members 31a and 31b, any material may be used insofar as it has good surface flatness and is non-conductive and substantially impermeable to water. For this purpose, it is appropriate to use, for example, a polyester such as polyethylene terephthalate or polycarbonate of bisphenol A, polymethyl methacrylate, polyethylene, polystyrene, a vinyl polymer such as polyvinyl chloride, a polyamide such as nylon, or a copolymer of the monomers mentioned above, e.g. vinylidene chloride-vinyl chloride copolymer The materials of the sheet members 31a and 31b may be identical or different. The front sheet member 31b (which is otherwise called the cover sheet) should preferably be as thin as practicable for enabling exposure for autoradiography therethrough. Thus the thickness of the front sheet member 31b is about 50 $\mu$m or less, preferably within the range of about 3 $\mu$m to about 50 $\mu$m, more preferably within the range of about 5 $\mu$m to about 40 $\mu$m. The thickness of the rear sheet member 31a may be equal to or different from the thickness of the front sheet member 31b, and may be within the range of about 5 $\mu$m to about 5 mm, preferably within the range of about 8 $\mu$m to about 3 mm.

The electrophoresis gel membrane 35 may be of any type insofar as electrophoresis can be effected therein and may be, for example, an acryl amide gel membrane, an agarose gel membrane, a starch gel membrane, an agar gel membrane, a cellulose acetate porous membrane, or a filter paper. Comb 36 is shown in the raised position, i.e., before contact with the upper edge of gel 35.

The electrophoresis gel sheet device 30 having the aforesaid configuration is sandwiched between the flat plate-like supporting members 21a and 21b. As shown in FIG. 1, a gap-forming member 40 having a square frame-like shape is disposed between the electrophoresis gel sheet device 30 and the flat plate-like supporting member 21b that is farther from the front frame 11. The gap-forming member 40 having this shape contacts only the edges of the electrophoresis gel sheet device 30 when the electrophoresis gel sheet device 30 is disposed between the flat plate-like supporting members 21a and 21b. Therefore, the central portion of the very thin and flexible sheet member 31b, i.e. the portion thereof facing the gel membrane 35 utilized for electrophoresis, is spaced from the supporting member 21b by a distance equal to the thickness of the gap-forming member 40. The thickness of the gap-forming member 40 should preferably be within the range of 0.15 mm to 0.6 mm, and may be 0.25 mm for example. Frame member 40 has an upper outer edge 40c and an upper inner edge 40d spaced downwardly from outer edge 40c to define the upper width of the frame. Edge 40d defines the upper edge of the central aperture of the frame.

Figure 4:
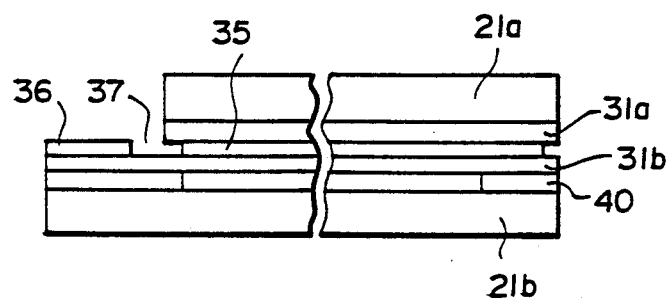
FIG. 4 is a vertical sectional view taken along line 4—4 of FIG. 1, showing the inventive electrophoresis sheet assembly employed in the embodiment of FIG. 1, and omitting, for purpose of clarity, upper portions of elements of the assembly to highlight cut-away portions thereof.

The flat plate-like supporting members 21a and 21b having the electrophoresis gel sheet device 30 disposed therebetween are secured to the front frame 11 by use of, for example, clips. Then, a buffer solution is introduced into the upper buffer solution vessel 2 and the lower buffer solution vessel 7, and water is introduced into the water vessel 5. A predetermined voltage is then applied across the external terminals 3a and 8a for carrying out electrophoresis. A cutaway portion 22 like the cutaway portion 11b at the upper end of the front frame 11 is formed at the upper end of the supporting member 21a closer to the front frame 11, and the buffer solution in the upper buffer solution vessel 2 contacts the upper edge of the gel membrane 35 via the cutaway portion 22. On the other hand, the lower end of the electrophoresis sheet assembly 20 is projected into the lower buffer solution vessel 7, so that the lower edge of the gel membrane 35 contacts the buffer solution in the lower buffer solution vessel 7. A shark's teeth comb 36 is inserted into an upper end 30b of the electrophoresis gel sheet device 30, thereby to form sample-pouring portions 37, 37, ... in contact with the upper edge of the gel membrane 35 as shown in FIG. 4. A sample liquid containing a protein, a nucleic acid, or a decomposition product thereof is poured into the sample-pouring portion 37 by use of a micro-syringe or the like. After the pouring of the sample liquid, the voltage is applied across the external terminals 3a and 8a acts on the gel membrane 35 via the buffer solution, and electrophoresis of the substance such as a protein or a nucleic acid poured into the sample-pouring portion 37 at the upper edge of the gel membrane 35 is carried out.

In the apparatus, since the electrophoresis sheet assembly 20 closes the front opening 11a of the water vessel 5, water in the water vessel 5 contacts the electrophoresis sheet assembly 20 at said section, whereby the temperature of the electrophoresis sheet assembly 20 is made uniform. Therefore, the temperature of the gel membrane 35 becomes substantially uniform, and it is possible to prevent a smiling effect, i.e. the effect that the migration speed of the charged substance becomes different between both edges of the gel membrane and the central portion thereof and the migration pattern is bent in a circular arc form.

As mentioned above, a small gap is formed between the central portion of the sheet member 31b and the supporting member 21b by the gap-forming member 40. Therefore, even though dust or the like is present on the surface of the sheet member 31b or on the surface of the supporting member 21b, there is no risk of the gel membrane 35 being dimpled by dust or the like. Accordingly, no distortion arises in the electrophoretic image.

As shown in FIG. 1, a mark 40b indicating the position to which the shark's teeth comb 36 is to be inserted is put on the upper edge portion of the gap-forming member 40. Therefore, when the shark's teeth comb 36 is to be inserted for forming the sample-pouring portions prior to the beginning of electrophoresis, the shark's teeth comb 36 can be inserted easily and reliably by matching the position thereof to the mark 40b. Also, a scale 40a indicating the vertical distance from the upper edge of the gel membrane may be provided along the vertical side of the gap-forming member 40, so that movement distances of migration patterns can be measured visually by the utilization of the scale 40a.

The present invention will be further illustrated by the following nonlimitative example.

EXAMPLE

The electrophoresis apparatus in accordance with the present invention was fabricated as described below.

A chemically strengthened glass plate having a length of 400 mm, a width of 200 mm and a thickness of 5 mm was placed horizontally, and an electrophoresis gel sheet device was overlaid on the glass plate. (Before overlaying the electrophoresis gel sheet device on the glass plate, 10 ml of water should preferably be poured onto the glass plate.) The electrophoresis gel sheet device was overlaid on the glass plate so that the cutaway side contacted the glass plate, and the upper end of the electrophoresis gel sheet device was aligned with the lower edge of the glass plate.

Then, a gap-forming member having a window frame-like shape was placed on the electrophoresis gel sheet device. The electrophoresis gel sheet device had such a configuration that the upper edge of the gel membrane in the electrophoresis gel sheet device was at the position spaced by 25 mm from the upper end of the electrophoresis gel sheet device. Also, the width of the upper side of the gap-forming member was 25 mm. Therefore, the upper edge of the gel membrane overlapped the inner edge of the upper side of the gap-forming member. That is, the upper inner edge 40d of frame member 40 was substantially aligned with the upper edge of the gel membrane 35, as shown in FIG. 4, or overlapped said gel membrane by an amount not more than 5 mm along the longitudinal extent of said membrane, when frame 40 is in place. The arrangement is such that the upper edge of the gel membrane 35 was spaced below the upper edge of sheet member 31b by a distance substantially equal to the upper width of frame 40. A second glass plate of the same type as the first mentioned glass plate was then overlaid carefully on the gap-forming member. The combination thus obtained was held together by clips and fitted to a predetermined position of the electrophoresis apparatus.

A buffer solution was poured into an upper buffer solution vessel and a lower buffer solution vessel, and the shark's teeth comb was inserted into the upper end of the electrophoresis gel sheet device until the teeth (protrusions) of the shark's teeth comb entered by approximately 0.5 mm into the gel membrane. Prior to the pouring of a sample liquid, a sample-pouring portion was washed with the buffer solution by use of a syringe. After the washing, a DNA sample was poured into the predetermined sample-pouring portion by the ordinary method.

The electrodes of the upper buffer solution vessel and the lower buffer solution vessel were connected to an electric power source, electrophoresis was carried out for four hours at 2,000 V. Then, a new sample-pouring portion was washed with the buffer solution, the same DNA sample as above was poured into the washed sample-pouring portion, and electrophoresis was carried out for two hours at 2,000 V.

Figure 5:
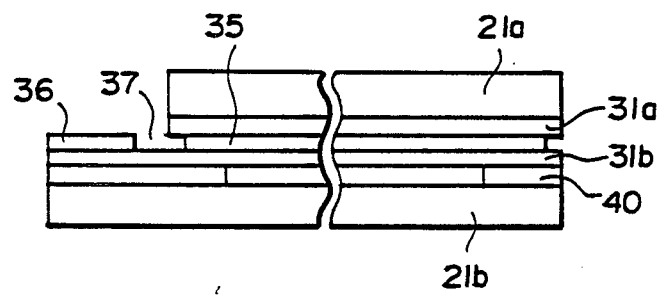
FIG. 5 is a vertical sectional view similar to FIG. 4 but not in accordance with the invention showing an electrophoresis sheet assembly for comparison.
Figure 6:
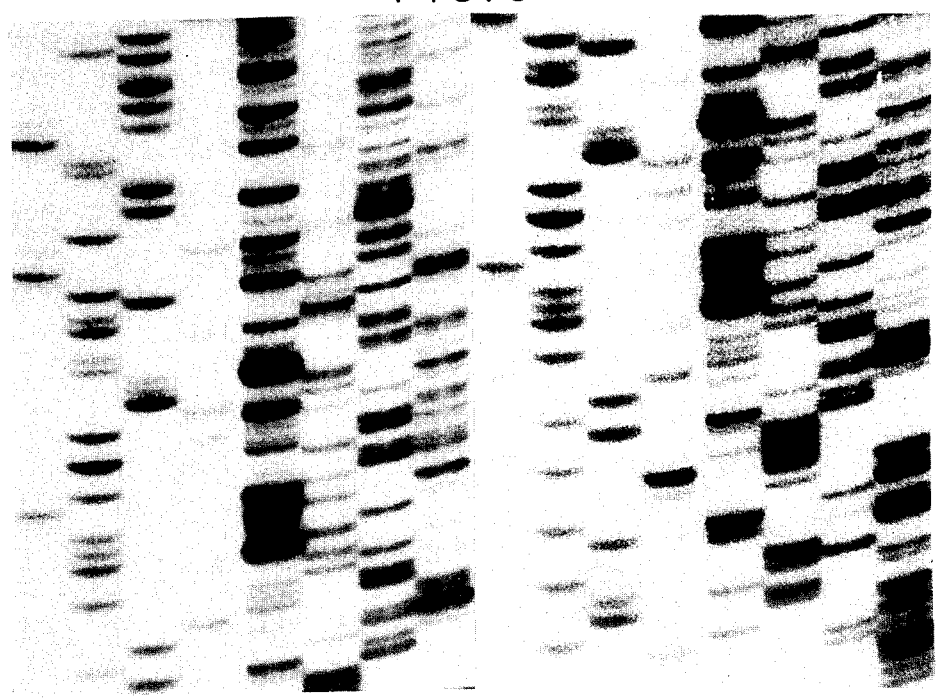
FIGS. 6 and 7 are radiographs showing major parts of electrophoretic images obtained by an example in accordance with the present invention and a comparative example.
Figure 7:
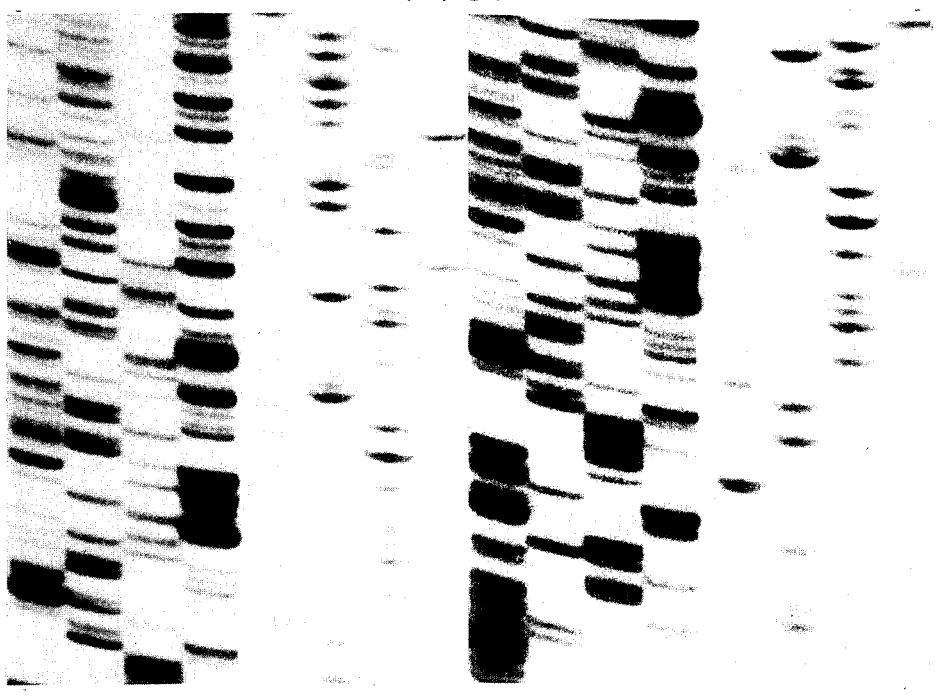

FIG. 6 shows an example of the results of the electrophoresis. FIG. 7 shows an example of the results of electrophoresis carried out for comparison by adjusting the width of the upper side of the gap-forming member to be 35 mm as shown in FIG. 5. The illustration of FIG. 5 is similar to that of FIG. 4 but is not in accordance with the invention. Thus, the upper side of the frame member 40 has an increased width causing an overlap of the frame width relative to the gel membrane of approximately 10 mm. As a result this excessive overlap makes it extremely difficult, if not impossible to consistently place the comb 36 in the same position so as to provide consistency in the size and location of the sample pouring portions. It is only when the overlap is 5 m or less, as shown in FIG. 4, that such consistency can be obtained. In FIG. 5, comb 36 is shown in the raised position, i.e., before contact with the upper edge of gel 35.

As is clear from FIG. 6, a substantially linear electrophoretic image is obtained with the electrophoresis apparatus in accordance with the present invention. On the other hand, with the comparative example using the conventional apparatus of FIG. 5, the electrophoretic image is distorted in a U-shape or in a V-shape as shown in FIG. 7.

We claim:

1. In an electrophoresis apparatus comprising two sheet members formed of a non-conductive organic polymer film and disposed to stand facing each other, spacers having predetermined thicknesses disposed at right and left edge portions between the two sheet members, and an eletrophoresis gel membrane of uniform thickness grasped between the two sheet members thereby forming an electrophoresis sheet, a pair of flat plate-like supporting members for supporting the electrophoresis sheet by sandwiching it between the supporting members, a frame-like spacer disposed between the electrophoresis sheet and one of the supporting members, and a flat plate-like comb member having teeth-like protrusions inserted in the top edge of the gel membrane to form sample liquid pouring apertures disposed along the membrane and defined by the top edge of the membrane, the upper edges of the spaced-apart sheet members, and the adjacent faces of the teeth-like protrusions, wherein the improvement comprises:

said frame-like spacer having an upper outer edge and an upper inner edge spaced downwardly from said upper outer edge to define the upper width of said frame, said frame being positioned with its upper inner edge substantially aligned with the upper edge of said gel membrane when said frame is in place.

2. An apparatus as defined in claim 1 wherein the upper edge of said gel membrane is spaced below the upper edge of one of said spaced-apart sheet members by a distance substantially equal to the upper width of said frame.

3. In an electrophoresis apparatus comprising two sheet members formed of a non-conductive organic polymer film and disposed to stand facing each other, spacers having predetermined thicknesses disposed at right and left edge portions between the two sheet members, and an eletrophoresis gel membrane of uniform thickness grasped between the two sheet members to form an electrophoresis sheet, a pair of flat plate-like supporting members for supporting the electrophoresis sheet by sandwiching it between the supporting members, a frame-like spacer disposed between the electrophoresis sheet and one of the supporting members, and a flat plate-like comb member having teeth-like protrusions inserted in the top edge of the gel membrane to form sample liquid pouring apertures disposed along the membrane and defined by the top edge of the membrane, the upper edges of the spaced-apart sheet members, and the adjacent faces of the teeth-like protrusions, wherein the improvement comprises:

said frame-like spacer having an upper outer edge and an upper inner edge spaced downwardly from said upper outer edge to define the upper width of said frame, a portion of said upper width overlapping an upper portion of said gel membrane by an amount no more than 5 mm along the longitudinal extent of said membrane.

4. An apparatus as defined in claim 3 wherein the extent of overlapping of said frame width relative to said gel membrane is 3 mm or less along the longitudinal extent of said membrane.

5. In an electrophoresis apparatus comprising two sheet members formed of a non-conductive organic polymer film and disposed to stand facing each other, spacers having predetermined thicknesses disposed at right and left edge portions between the two sheet members, and an eletrophoresis gel membrane of uniform thickness grasped between the two sheet members to form an electrophoresis sheet, a pair of flat plate-like supporting members for supporting the electrophoresis sheet by sandwiching it between the supporting members, a frame-like spacer disposed between the electrophoresis sheet and one of the supporting members, and a flat plate-like comb member having teeth-like protrusions inserted in the top edge of the gel membrane to form sample liquid pouring apertures disposed along the membrane and defined by the top edge of the membrane, the upper edges of the spaced-apart sheet members, and the adjacent faces of the teeth-like protrusions, wherein the improvement comprises:

said frame-like spacer having marking indicia adapted to determine the position at which said comb is to be inserted downwardly in said gel membrane, and said frame-like spacer having an upper outer edge and an upper inner edge spaced downwardly from said upper outer edge to define the upper width of said frame, said upper inner edge of said frame and the upper edge of said membrane being in a fixed position and in sufficiently close proximity to each other such that said comb can be repeatedly accurately positioned in said gel membrane to prevent sample liquid poured in one aperture from invading an adjacent pouring aperture and to prevent upward swelling of said gel membrane during electrophoresis.

6. An apparatus as defined in claim 1, 2, 3, 4 or 5 wherein said comb is formed of a polyethylene terephthalate film.

7. An apparatus as defined in claim 1, 2, 3, 4 or 5 wherein said comb is formed of a semitransparent polyethylene terephtalate film.

8. An apparatus as defined in claim 1, 2, 3, 4 or 5 wherein said electrophoresis gel consists of polyacrylamide.

9. An apparatus as defined in claim 1, 2, 3, 4 or 5 wherein said spacers disposed between said sheet members have a thickness greater than the corresponding thickness of said gel membrane, and the thickness d of said comb is greater than the corresponding thickness of said spacers by 20 $\mu$m or less.

10. An apparatus as defined in claim 1, 2, 3, 4 or 5 wherein the thickness d of said comb and the thickness G of said gel membrane satisfy the relationship of $$G \times 1.1 < d < G + 50$$

where the unit is $\mu$m and G is less than 500.

11. An apparatus as defined in claim 1, 2, 3, 4 or 5 wherein said frame-like spacer member is formed of an electrically insulating flexible thin sheet.

12. An apparatus as defined in claim 1, 2, 3, 4 or 5 wherein the thickness of said frame-like spacer member is within the range of 0.1 mm to 0.6 mm.

* * * * *